US008795383B2

(12) United States Patent
Alvarado

(10) Patent No.: US 8,795,383 B2
(45) Date of Patent: Aug. 5, 2014

(54) LAPAROSCOPIC INGUINAL HERNIA PROSTHESIS

(76) Inventor: Alfredo Alvarado, Weston, FL (US)

( * ) Notice: Subject to any disclaimer, the term of this patent is extended or adjusted under 35 U.S.C. 154(b) by 973 days.

(21) Appl. No.: 11/151,677

(22) Filed: Jun. 13, 2005

(65) Prior Publication Data

US 2006/0015143 A1    Jan. 19, 2006

Related U.S. Application Data

(60) Provisional application No. 60/588,773, filed on Jul. 19, 2004.

(51) Int. Cl.
*A61F 2/02* (2006.01)

(52) U.S. Cl.
USPC .......................... 623/23.72; 606/151; 606/213

(58) Field of Classification Search
USPC ..................... 623/23.72, 11.11; 606/213, 151
See application file for complete search history.

(56) References Cited

U.S. PATENT DOCUMENTS

| | | | |
|---|---|---|---|
| 4,769,038 A | | 9/1988 | Bendavid |
| 5,147,374 A | * | 9/1992 | Fernandez ..................... 606/151 |
| 5,254,133 A | | 10/1993 | Seid |
| 5,356,432 A | * | 10/1994 | Rutkow et al. ............. 623/23.72 |
| 5,456,720 A | * | 10/1995 | Schultz et al. ............. 623/23.64 |
| 5,593,441 A | | 1/1997 | Lichtenstein et al. |
| 5,725,577 A | | 3/1998 | Saxon |
| 5,743,917 A | | 4/1998 | Saxon |
| 5,916,225 A | * | 6/1999 | Kugel ........................... 606/151 |
| 6,113,641 A | * | 9/2000 | Leroy et al. ................ 623/23.75 |
| 6,120,539 A | | 9/2000 | Eldridge et al. |
| 6,171,318 B1 | * | 1/2001 | Kugel et al. .................... 606/151 |
| 6,180,848 B1 | * | 1/2001 | Flament et al. ............. 623/11.11 |
| 6,241,768 B1 | * | 6/2001 | Agarwal et al. ............. 623/11.11 |
| 6,267,772 B1 | * | 7/2001 | Mulhauser et al. ........... 606/151 |
| 6,270,530 B1 | | 8/2001 | Eldridge |
| 6,596,002 B2 | * | 7/2003 | Therin et al. ................... 606/151 |
| 7,404,819 B1 | * | 7/2008 | Darios et al. ................... 606/151 |
| 2002/0026092 A1 | * | 2/2002 | Buckberg et al. ............... 600/37 |
| 2002/0049503 A1 | * | 4/2002 | Milbocker ................. 623/23.72 |
| 2002/0120337 A1 | * | 8/2002 | Cauthen ..................... 623/17.16 |

(Continued)

*Primary Examiner* — Kathleen Holwerda
*Assistant Examiner* — Sarah Simpson
(74) *Attorney, Agent, or Firm* — Mark D. Bowen; Malin Haley DiMaggio & Bowen, P.A.

(57) ABSTRACT

An improved composite prosthesis for laparoscopic repair of inguinal or femoral hernias, and also for the laparoscopic repair of large incisional ventral hernias incorporates two different layers, namely an upper layer made of polypropylene mesh to promote tissue ingrowth, and a lower layer formed with an adhesion barrier material to prevent adhesions to the intestines. Both layers are secured together with a highly visible dark seam at the perimeter of the prosthesis to assist the surgeon in visualizing the peripheral edge. The lower layer is slightly larger than the polypropylene mesh so there is an adhesion barrier edge around the prosthesis to conceal the edges of the polypropylene mesh. The upper layer includes a guiding cone to facilitate placement of the prosthesis at the exact center of the hernial defect. The base of this cone is attached to the central part of the prosthesis, and the apex of the cone will be attached later to a guiding thread that is inserted to from the outside of the abdomen using a long straight needle through the skin and hernial sac. Furthermore the laparoscopic hernia prosthesis lower layer is provided with a bounding rim to guide the tip of the spiral tacker to the very edges of the prosthesis in order to stretch the prosthesis in place, and also to conceal the staples or tacks.

11 Claims, 2 Drawing Sheets

(56) References Cited

U.S. PATENT DOCUMENTS

| | | | |
|---|---|---|---|
| 2002/0147457 A1* | 10/2002 | Rousseau | 606/157 |
| 2003/0181988 A1* | 9/2003 | Rousseau | 623/23.72 |
| 2003/0187516 A1 | 10/2003 | Amid | |
| 2003/0212461 A1* | 11/2003 | Vadurro et al. | 623/23.64 |
| 2003/0212462 A1 | 11/2003 | Gryska | |
| 2004/0087980 A1* | 5/2004 | Ford et al. | 606/151 |
| 2006/0253203 A1* | 11/2006 | Alvarado | 623/23.74 |
| 2006/0259074 A1* | 11/2006 | Kelleher et al. | 606/213 |
| 2007/0032881 A1* | 2/2007 | Browning | 623/23.72 |
| 2007/0299538 A1* | 12/2007 | Roeber | 623/23.72 |

* cited by examiner

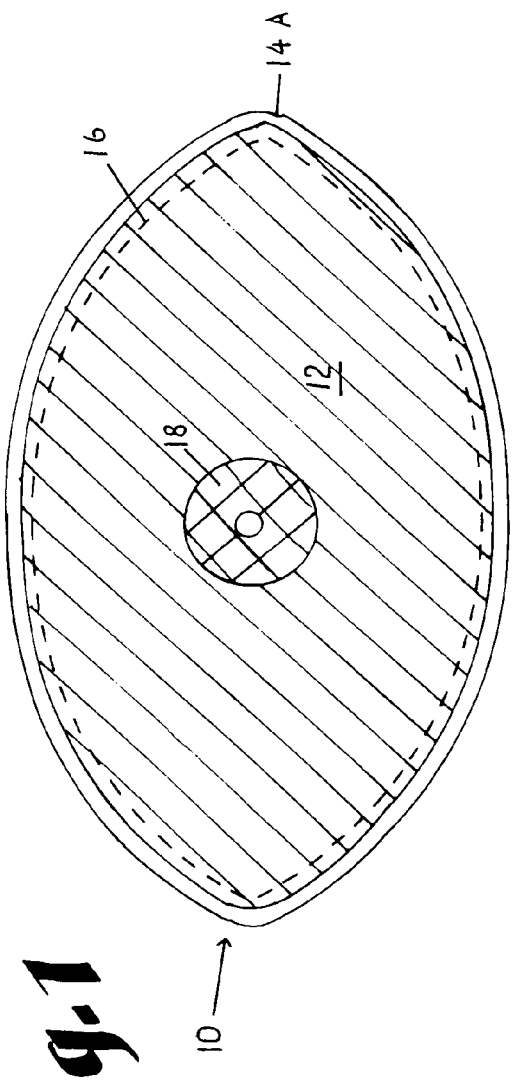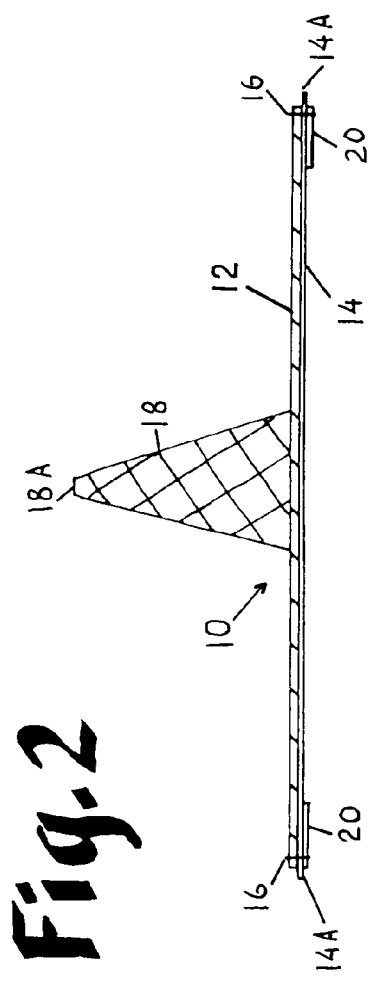

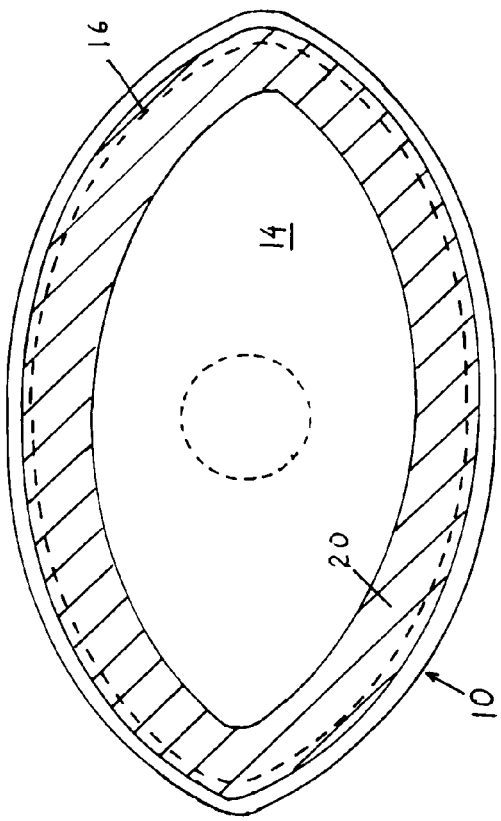
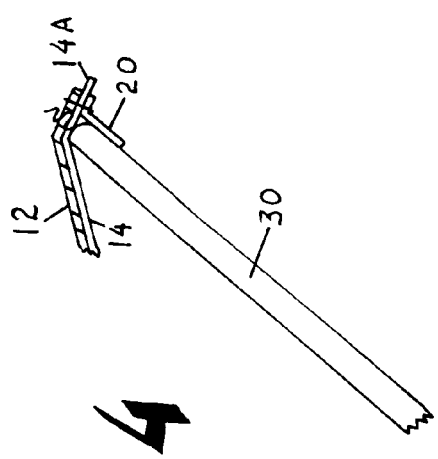

LAPAROSCOPIC INGUINAL HERNIA PROSTHESIS

CROSS REFERENCE TO RELATED APPLICATIONS

This application claims the benefit of provisional U.S. Patent Application Ser. No. 60/588,773, filed Jul. 19, 2004.

STATEMENT REGARDING FEDERALLY SPONSORED RESEARCH OR DEVELOPMENT

N/A

COPYRIGHT NOTICE

A portion of the disclosure of this patent document contains material that is subject to copyright protection. The copyright owner has no objection to the facsimile reproduction by anyone of the patent document or patent disclosure as it appears in the Patent and Trademark Office patent file or records, but otherwise reserves all copyrights rights whatsoever.

BACKGROUND OF THE INVENTION

1. Field of the Invention

The present invention relates to surgical implants for repair of inguinal and femoral hernias and also for the repair of large ventral or incisional hernias.

2. Description of Related Art

At present time there are three types of laparoscopic inguinal repairs: 1) the transabdominal preperitoneal repair or TAPP, 2) intraperitoneal onlay mesh repair or IPOM, and 3) the totally extraperitoneal laparoscopic repair or TEP.

The TAPP and TEP procedures require extensive dissection of the preperitoneal space with the inherent risks of nerve or vascular injuries and a high incidence of hematoma or seroma formation. On the other hand the IPOM procedure is very appealing because of its speed and simplicity and also because it eliminates the risks related to the preperitoneal dissection. The only disadvantage is the possibility of complications related to adhesion formation but this can be overcome by using adhesion barrier materials such as expanded polytetraetylene (ePTFE).

In the majority of the cases the implantable prosthesis consists of a composite patch made of a physical barrier to prevent formation of adhesions on the peritoneal side, and a knitted polypropylene monofilament mesh on the outer side to promote ingrowth and incorporation of the mesh into the abdominal wall such as Composix from Bard, Inc. and Sepramesh from Genzyme, Inc. A different type of prosthesis is made of expanded polytetrafluoroethylene with a smooth surface on one side, and a corrugated surface on the other side (Goretex Dual Mesh). The smooth side faces the intestine and serves as an adhesion barrier, while the corrugated surface is applied against the abdominal wall to promotes fixation via cellular and collagen ingrowth.

U.S. Pat. No. 5,916,225, issued to Kugel, discloses a hernia patch having a first layer of inert synthetic mesh material selectively sized and shaped to extend across and beyond a hernia, and a second layer of inert synthetic mesh material overlies the first layer to create a generally planar configuration for the patch. The first and second layers are joined together by a seam which defines a periphery of a pouch between the layers. One of the layers has a border which extends beyond the seam and which has a free outer edge. An access slit is formed in one of the layers for insertion of a finger of a surgeon into the pouch to allow the surgeon to deform the planar configuration of the patch to facilitate insertion of the patch into the patient and to position the patch across the hernia.

U.S. Pat. No. 5,593,441, issued to Lichtenstein et al., discloses a composite prosthesis and method for limiting the incidence of postoperative adhesions. The composite includes a mesh fabric and a barrier which prevents exposure of the mesh fabric to areas of potential adhesion. The interstices of the mesh fabric are infiltrated by tissue which secures the prosthesis in place. The composite is positioned with the barrier relative to the region of potential adhesion, such as the abdominal viscera.

U.S. Pat. No. 5,147,374, issued to Fernandez, discloses a patch made from a rolled up first flat sheet of polypropylene or polytetrafluroethylene surgical mesh. One end of the rolled up mesh has multiple slits to provide multiple flared out flaps stitched to a second flat sheet of surgical mesh. The patch is compressed into a longitudinal cylindrical structure and is inserted through a trocar into an opening of a hernia. The rolled up first flat sheet is inserted through the opening and the flaps and second flat sheet are stapled to the patient's tissue adjacent the opening.

Other hernia repair devices are disclosed in U.S. Application Publication No. 2003/0181988 (Rousseau), 2003/0187516 (Amid et al.), U.S. Pat. Nos. 6,120,530 (Eldridge et al.), 4,769,038 (Bendavid et al.), 5,725,577 and 5,743,917 (Saxon).

During the last few years, laparoscopic inguinal repairs have been gaining ground among surgeons as compared to the open tension-free repairs particularly for the repair of recurrent or bilateral hernias. However the laparoscopic repairs involve the use of general anesthesia and expensive laparoscopic instruments and some times very expensive prosthetic materials. Furthermore the laparoscopic transabdominal techniques are associated with some risk of visceral or vascular injuries related to the insertion of ports but this risk is minimized due to the experience gained by surgeons during the last two decades.

The implantable prosthesis devices disclosed in the art are burdened by a number of disadvantages and are often not well suited for use in laparoscopic hernial repairs. Accordingly, there exists a need for an improved implantable prosthesis for laparoscopic repair of inguinal or femoral hernias, and also for the laparoscopic repair of large incisional ventral hernias. There further exists a need for such a prosthesis that assists the surgeon in guiding the prosthesis into position upon insertion. A need also exists for a laparoscopically implantable prosthesis wherein fixation of the prosthesis can be accomplished precisely along the peripheral edge of the prosthesis using a spiral tacker.

BRIEF SUMMARY OF THE INVENTION

The present invention overcomes the limitations and disadvantages present in the art by providing an improved composite prosthesis for laparoscopic repair of inguinal or femoral hernias, and also for the laparoscopic repair of large incisional ventral hernias. This prosthesis incorporates two different layers, namely an upper layer made of polypropylene mesh to promote tissue ingrowth, and a lower layer formed with an adhesion barrier material to prevent adhesions to the intestines. Both layers are secured together with a highly visible dark seam at the perimeter of the prosthesis. The use of a dark seam makes it easier to visualize the edges of the prosthesis. The lower layer is slightly larger than the polypropylene mesh so there is an adhesion barrier edge around the prosthesis to conceal the edges of the polypropylene mesh. The inguinal hernia prosthesis is provided with a guiding cone made of the same polypropylene material to facilitate placement of the prosthesis at the exact center of the hernial defect. The base of this cone is attached to the central part of the prosthesis, and the apex of the cone will be attached later to a guiding thread that is inserted to from the outside of the abdomen using a long straight needle through the skin and hernial sac. Furthermore the laparoscopic hernia prosthesis lower layer is provided with a bounding rim made of the same material as the adhesion barrier. The purpose of this rim is to guide the tip of the spiral tacker to the very edges of the prosthesis in order to stretch the prosthesis in place, and also to conceal the staples or tacks.

Accordingly, it is an object of the present invention to provide an improved implantable hernial prosthesis.

Another object of the present invention is to provide a hernial prosthesis adapted such that the prosthesis may be precisely and efficiently positioned at the exact center of the hernial defect.

Still another object of the present invention is to provide a hernial prosthesis wherein the staples or tacks are covered by one layer of the prosthesis.

In accordance with these and other objects, which will become apparent hereinafter, the instant invention will now be described with particular reference to the accompanying drawings.

BRIEF DESCRIPTION OF THE SEVERAL VIEWS OF THE DRAWINGS

FIG. 1 is a top view of a laparoscopic inguinal hernia prosthesis according to the present invention;

FIG. 2 is a side view thereof;

FIG. 3 is a bottom view thereof; and

FIG. 4 illustrates affixation of the prosthesis using a spiral tack mechanism.

DETAILED DESCRIPTION OF THE INVENTION

With reference now to the drawings, FIGS. 1-4, depict a preferred embodiment of a laparoscopic inguinal hernia prosthesis, generally referenced as 10, in accordance with the present invention. Prosthesis 10 comprises a composite prosthesis for laparoscopic repair of inguinal or femoral hernias, and also for the laparoscopic repair of large incisional ventral hernias. As best seen in FIG. 1, prosthesis 10 is fabricated in a semi-elliptical shape that has been found to adapt quite well to the anatomy of the inguinal area and facilitates the fixing of the prosthesis to the Cooper's ligament.

Prosthesis 10 includes two different layers, namely an upper layer 12 and a lower layer 14. Upper layer 12 is preferably fabricated from polypropylene mesh to promote tissue ingrowth. Lower layer 14 is preferably fabricated a generally smooth sheet of an adhesion barrier material to prevent adhesion to the intestines. Upper layer 12 and lower layer 14 are secured together with a dark seam 16 proximal the perimeter of prosthesis 10. The seam preferably is formed with a black color to make it easier to visualize the edge of prosthesis 10. As best depicted in FIGS. 1 and 2, lower layer 14 is slightly larger than the polypropylene mesh upper layer 12 forming an adhesion barrier edge 14A around prosthesis 10 to conceal the edges of the polypropylene mesh upper layer 12.

As best seen in FIG. 2, inguinal hernia prosthesis 10, and particularly upper layer 12, includes a projecting guiding cone 18 having an apex 18A. Guiding cone 18 is preferably made of the same polypropylene material as upper layer 12 and functions to facilitate placement of the prosthesis at the exact center of the hernial defect by projecting through the center of the defect upon insertion and positioning of prosthesis 10. The base of guiding cone 18 is attached to the central part of the prosthesis upper layer 12, and the apex of the cone will be attached to a guiding thread that is inserted from the outside of the abdomen using a long straight needle through the skin and hernial sac.

As illustrated in FIGS. 3 and 4, laparoscopic hernia prosthesis 10 is further provided with a bounding rim 20. Bounding rim 20 is affixed to lower layer 14 along the peripheral edge thereof, and is preferably fabricated from the same material as the lower layer adhesion barrier. Bounding rim 20 functions as a stop to assist in guiding the tip of a spiral tacker or stapler into the very edges of the prosthesis in order to stretch the prosthesis in place, and also to conceal the staples or tacks. FIG. 4 is a partial side view depicting a spiral tacker 30 positioned between bounding rim 20 and prosthesis lower layer 14 to stretch the prosthesis in place and affix prosthesis 10 with the aid of spiral tacker 30, or alternatively with a stapler (not shown).

Method of Insertion

The pneumoperitoneum is established by inserting a Verres needle at the upper margin of the umbilicus and then a 5 mm cannula is inserted in the left side of the abdomen lateral to the rectus muscle at the level of the umbilicus. Then the peritoneal cavity is inspected with a 5 mm laparoscope to visualize the hernial defect. If the defect is too large or if the hernia is of the direct type, an alternative method of repair, such as the Kugel patch technique or a conventional open repair is recommended. This decision is made based on the high possibility of recurrence with those types of hernial defects. If the hernia is of the indirect type or if it is recurrent or bilateral, the surgeon can proceed with the intraperitoneal onlay technique. If this is the case a 5-12 mm cannula, preferably the VersaStep Plus port from the U.S. Surgical Instruments, is inserted at the upper margin of the umbilicus. The right-handed surgeon can work very easily standing on the left side of the patient no matter which side the hernia is located.

A 22 gauge spinal needle, as a pilot needle, is inserted through the skin and hernial sac just below the external inguinal ring and directed toward the neck of the sac under direct vision. Then a 4" straight needle with a 3-0 polyglactin thread is inserted parallel to the spinal needle. The spinal needle is removed and reinserted in the midline just above the pubis in order to establish a point of reference inside the abdomen. The straight needle is retrieved with a 5 mm grasper inserted through the umbilical port and then attached to the apex 18A of guide cone 18 of the prosthesis.

Laparoscopic hernia prosthesis 10 is pushed through the 12 mm cannula by rolling up the prosthesis longitudinally on a long jaw grasper and with the polypropylene mesh and guiding cone inside the prosthesis. Once in the abdomen, the prosthesis is released from the grasper and then guided into the hernial sac by making gentle traction on the polyglactin thread. Prosthesis 10 is spread with a grasper and oriented parallel to the inguinal ligament and then held in position by maintaining traction on the thread attached to the cone. Finally, prosthesis 10 is secured in place using a 5 mm stapler or spiral tacker 30 that is inserted through the 5 mm port. The tip of instrument, such as spiral tacker 30, is slipped under bounding rim 20 starting at the upper edge of the prosthesis. Extreme care should be taken to avoid the so-called "triangle of doom and pain" at the lower edge of the prosthesis where no tacks should be applied. The guiding thread is anchored under the skin by making four passes with a straight needle in a zig-zag manner but without tying the end of the thread because this may produce some pain due to post-operative local swelling. The incisions of the abdominal wall are closed in the usual manner.

Among the significant advantages provided by a prosthesis 10 according to the present invention are the following:

1. Laparoscopic inguinal hernial prosthesis 10 may be inserted into the abdominal cavity through a 12 mm cannula by rolling it on a long jaw grasper;

2. Hernial prosthesis guiding cone 18 can be positioned into the hernial sac by using a guiding thread that is inserted with a needle from outside of the abdomen through the skin and hernial sac;

3. The edges of the polypropylene mesh are concealed by a lower adhesion barrier edge 14A to avoid adhesions to the mesh;

4. Bounding rim 20 of the prosthesis will lead the tip of spiral tacker 30, or stapler, into the edges of prosthesis 10 to expand the prosthesis in place, and further functions to conceal the staples or tacks;

5. The polypropylene mesh forming upper layer 12 provides effective tissue ingrowth into the peritoneal layer and the adhesion barrier forming lower layer 14 reduces the risk of adhesions to the prosthesis;

6. The particular semi-elliptical shape of prosthesis 10 adapts quite well to the anatomy of the inguinal area and facilitates the fixing of the prosthesis to the Cooper's ligament.

7. In the vast majority of cases there is no need to dissect the tissues adjacent to the hernial sac making the procedure safer and faster and at the same time avoiding complications such as bleeding or formation of hematomas or seromas.

8. The whole procedure requires only two ports: one 12 mm port inserted in the umbilical area, and a 5 mm port inserted in the left side of the abdomen. The surgeon always works on the left side of the patient, and the scrub nurse works on the right side.

Finally, laparoscopic hernia prosthesis 10 of the present invention is suitable for use in other applications. For example, laparoscopic hernia prosthesis 10 can be modified for the repair of large ventral or recurrent incisional hernias by changing its shape and size. In this case an oval shape should be preferable, and the size of the prosthesis should be proportional to the hernial defect. In addition, guiding cone 18 can be eliminated but the bounding rim should remain the same in order to facilitate the spreading and fixation of the prosthesis as mentioned before.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. A prosthesis for repair of hernial defects by laparoscopic insertion within a patient, said prosthesis comprising:
   a prosthesis body sized and shaped for laparoscopic insertion in covering relation with a hernial defect;
   said prosthesis body including connected upper and lower layers formed of synthetic material, said upper layer disposed toward the patient's abdominal wall and said lower layer disposed toward the patient's intestines when said prosthesis body is properly surgically positioned;
   said lower layer comprising a solid sheet adhesion barrier generally devoid of openings;
   a generally hollow guiding cone having a base connected to said upper layer and projecting upward therefrom terminating in an apex;
   a flexible bounding rim flap affixed to said lower layer on the side thereof opposite of said upper layer and along a peripheral edge thereof and disposed in substantially adjacent overlapping relation with said lower layer on the side thereof opposite of said upper layer;
   said bounding rim flap having an outer edge affixed to said lower layer in proximity to the peripheral edge thereof such that said bounding rim flap functions as a stop to assist in guiding the tip of a surgical instrument inserted between said bounding rim flap and said lower layer to the peripheral edge of the prosthesis in order to stretch the prosthesis in place and to overlap surgical fasteners, and an unsecured inner edge, such that said unsecured inner edge is oriented toward the center of the prosthesis.

2. A prosthesis according to claim 1, wherein said upper layer comprises a mesh bounded by a peripheral edge.

3. A prosthesis according to claim 2, wherein said lower layer extends beyond the peripheral edge of said upper layer.

4. A prosthesis according to claim 1, wherein said upper and lower layers are connected by a peripheral seam.

5. A prosthesis according to claim 4, wherein said seam is defined by a dark color.

6. A prosthesis for repair of hernial defects by laparoscopic insertion within a patient for affixation in the patient's abdominal cavity disposed between the intestines and the peritoneal layer, said prosthesis comprising:
   an upper layer of synthetic mesh material, said upper layer having a peripheral edge;
   a lower layer of synthetic material connected to said upper layer, said lower layer having a peripheral edge extending beyond said upper layer peripheral edge, said lower layer generally devoid of openings;
   said upper layer disposed toward the patient's abdominal wall and said lower layer disposed toward the patient's intestines when said prosthesis body is properly surgically positioned
   a guiding cone having a base connected to said upper layer and projecting therefrom; and
   a bounding rim disposed on said lower layer on the side thereof opposite said upper layer and extending along substantially the entire peripheral lower layer edge;
   said bounding rim including a flexible flap having a radially outer portion attached to the lower side of said lower layer and an unsecured radially inner portion, such that said unsecured radially inner portion is oriented toward the center of the prosthesis;
   said prosthesis upper layer disposed facing the patient's peritoneal layer and said prosthesis lower layer disposed facing the patient's intestines when surgically inserted into the patient;
   said attached radially outer portion of said flap functioning as a stop to assist in guiding the tip of a surgical instrument inserted between said flap and said lower layer to the peripheral edge of the prosthesis in order to stretch the prosthesis in place and to overlappingly conceal surgically implanted staples or tacks used to affix the prosthesis to the patient.

7. A prosthesis according to claim 6, wherein said upper layer comprises mesh selected from the group consisting of polypropylene and polyester.

8. A prosthesis according to claim 6, wherein said lower layer comprises generally solid sheet of expanded polytetrafluoroethylene.

9. A prosthesis according to claim 6, wherein said upper and lower layers are connected by a seam.

10. A prosthesis according to claim 9, wherein said seam is formed by stitched thread.

11. A prosthesis according to claim 10, wherein said thread is dark in color.

* * * * *